(12) United States Patent
Hein, Jr. et al.

(10) Patent No.: US 10,470,698 B2
(45) Date of Patent: *Nov. 12, 2019

(54) ALLERGY TESTING DEVICE AND METHOD OF TESTING FOR ALLERGIES

(71) Applicant: Lincoln Diagnostics, Inc., Decatur, IL (US)

(72) Inventors: Gary L. Hein, Jr., Decatur, IL (US); Douglas S. Hein, Decatur, IL (US)

(73) Assignee: Lincoln Diagnostics, Inc., Decatur, IL (US)

( * ) Notice: Subject to any disclaimer, the term of this patent is extended or adjusted under 35 U.S.C. 154(b) by 175 days.

This patent is subject to a terminal disclaimer.

(21) Appl. No.: 15/362,404

(22) Filed: Nov. 28, 2016

(65) Prior Publication Data

US 2017/0071527 A1    Mar. 16, 2017

Related U.S. Application Data

(63) Continuation of application No. 14/689,686, filed on Apr. 17, 2015, now Pat. No. 9,504,418, which is a
(Continued)

(51) Int. Cl.
*A61B 5/00* (2006.01)

(52) U.S. Cl.
CPC .............. *A61B 5/411* (2013.01); *A61B 5/445* (2013.01)

(58) Field of Classification Search
CPC . A61B 17/205; A61B 5/411; A61B 5/150022; A61B 5/441; A61M 5/422
See application file for complete search history.

(56) References Cited

U.S. PATENT DOCUMENTS 2,522,309 A   8/1950  Simon
2,743,723 A   5/1956  Hein
(Continued)

FOREIGN PATENT DOCUMENTS

CN    2129604 Y    4/1993
CN    2750778 Y    1/2006
(Continued)

OTHER PUBLICATIONS

Inside Dentistry: A Relatively "Painless" Way to Avoid Pain: Jan. 2007, vol. 3, Iss. 1.
(Continued)

*Primary Examiner* — Patrick Fernandes
(74) *Attorney, Agent, or Firm* — Banner & Witcoff, Ltd.

(57) ABSTRACT

An allergy testing system comprises a skin test device having a grip portion for holding the device. One or more legs extend from the grip, and each leg is oriented to interact with a well containing a potential allergen. Each leg has a test head, and each test head has a plurality of elongated spike members. The elongated spike members have a sharp end configured to receive the potential allergen from a well and to puncture a patient's skin. In addition, each test head has at least one touch activator. The touch activator is longer than the plurality of elongated spike members, such that during an allergy test, the touch activator comes into contact with the skin prior to the elongated spike members, causing the touch activators to activate nerve tissue that blocks transmission of pain, resulting in a reduction of pain and/or discomfort during testing.

21 Claims, 7 Drawing Sheets

Related U.S. Application Data continuation of application No. 13/925,258, filed on Jun. 24, 2013, now Pat. No. 9,011,350, which is a continuation-in-part of application No. 13/308,111, filed on Nov. 30, 2011, now Pat. No. 8,469,900.

(56) References Cited

U.S. PATENT DOCUMENTS

| | | |
|---|---|---|
| 2,841,138 A | 7/1958 | Laub |
| 3,221,739 A | 12/1965 | Rosenthal |
| 3,246,647 A | 4/1966 | Taylor et al. |
| 3,322,121 A | 5/1967 | Banker |
| 3,470,011 A | 9/1969 | Szumski |
| 3,512,520 A | 5/1970 | Cowan |
| 3,556,080 A | 1/1971 | Hein |
| 3,596,660 A | 8/1971 | Melone |
| 3,688,764 A | 9/1972 | Reed |
| 3,921,804 A | 11/1975 | Tester |
| 4,109,655 A | 8/1978 | Chacomac |
| 4,205,689 A | 6/1980 | Brennan |
| 4,222,392 A | 9/1980 | Brennan |
| 4,237,906 A | 12/1980 | Havstad et al. |
| 4,270,548 A | 6/1981 | Brennan |
| 4,292,979 A | 10/1981 | Inglefield, Jr. et al. |
| 4,304,241 A | 12/1981 | Brennan |
| 4,319,584 A | 3/1982 | McCall |
| 4,453,926 A | 6/1984 | Galy |
| 4,607,632 A | 8/1986 | Brennan et al. |
| 4,759,755 A | 7/1988 | Hein et al. |
| D297,052 S | 8/1988 | Galy |
| 4,802,493 A | 2/1989 | Maganias |
| 5,076,282 A | 12/1991 | Fishman et al. |
| 5,139,029 A | 8/1992 | Fishman et al. |
| 5,154,181 A | 10/1992 | Fishman |
| 5,335,670 A | 8/1994 | Fishman |
| 5,396,989 A | 3/1995 | Hein |
| D360,945 S | 8/1995 | Baldwin |
| 5,441,490 A | 8/1995 | Svedman |
| 5,538,134 A | 7/1996 | Pitesky |
| 5,551,441 A | 9/1996 | Pitesky |
| 5,588,441 A | 12/1996 | Fishman |
| 5,605,160 A | 2/1997 | Fishman |
| 5,632,728 A | 5/1997 | Hein |
| 5,647,371 A | 7/1997 | White, Jr. et al. |
| 5,671,753 A | 9/1997 | Pitesky |
| 5,673,705 A | 10/1997 | Pitesky |
| 5,692,518 A | 12/1997 | Baker et al. |
| 5,735,288 A | 4/1998 | Fishman |
| 5,738,108 A | 4/1998 | Hein |
| 5,746,700 A | 5/1998 | Hsiao |
| 5,749,836 A * | 5/1998 | Hsiao ............... A61B 10/0035 600/556 |
| 5,792,071 A | 8/1998 | Hein |
| 5,820,562 A | 10/1998 | Hsiao |
| 5,871,452 A | 2/1999 | Baker et al. |
| 5,931,794 A | 8/1999 | Pitesky |
| 5,944,671 A | 8/1999 | White, Jr. |
| 5,964,729 A | 10/1999 | Choi et al. |
| 6,024,706 A | 2/2000 | Hsiao |
| D426,305 S | 6/2000 | Hein |
| 6,077,229 A | 6/2000 | Pitesky |
| 6,095,988 A | 8/2000 | Doll et al. |
| 6,206,838 B1 | 3/2001 | Doll et al. |
| 6,221,027 B1 | 4/2001 | Pitesky |
| 6,231,531 B1 | 5/2001 | Lum et al. |
| 6,258,041 B1 | 7/2001 | Pitesky |
| 6,306,152 B1 | 10/2001 | Verdonk et al. |
| 6,554,777 B1 | 4/2003 | Hein, Jr. |
| 6,611,707 B1 | 8/2003 | Prausnitz et al. |
| 6,629,949 B1 | 10/2003 | Douglas |
| 6,743,211 B1 | 6/2004 | Prausnitz et al. |
| 6,902,554 B2 | 6/2005 | Huttner |
| 7,186,235 B2 | 3/2007 | Martin et al. |
| 7,226,439 B2 | 6/2007 | Prausnitz et al. |
| 7,422,567 B2 | 9/2008 | Lastovich et al. |
| 7,631,765 B2 | 12/2009 | Hein et al. |
| 7,740,600 B2 | 6/2010 | Slatkine et al. |
| D624,195 S | 9/2010 | Hein, Jr. et al. |
| D629,518 S | 12/2010 | Hein, Jr. et al. |
| 7,922,672 B2 | 4/2011 | Hein, Jr. et al. |
| 7,942,827 B2 | 5/2011 | Mir et al. |
| 8,206,336 B2 | 6/2012 | Shantha |
| 9,011,350 B2 | 4/2015 | Hein, Jr. et al. |
| 9,149,618 B2 | 10/2015 | Xu |
| 9,782,114 B2 | 10/2017 | Reynolds et al. |
| 9,795,334 B2 | 10/2017 | Freeman et al. |
| 2004/0162573 A1 | 8/2004 | Kheiri |
| 2004/0254599 A1 | 12/2004 | Lipoma et al. |
| 2005/0054981 A1 | 3/2005 | Romano |
| 2005/0137531 A1 | 6/2005 | Prausnitz et al. |
| 2005/0149145 A1 | 7/2005 | Coulter |
| 2005/0177071 A1 | 8/2005 | Nakayama et al. |
| 2006/0178615 A1 | 8/2006 | Ronborg et al. |
| 2006/0270998 A1 | 11/2006 | Marti |
| 2007/0232956 A1 | 10/2007 | Harman et al. |
| 2007/0299361 A1 | 12/2007 | Hein et al. |
| 2008/0058848 A1 | 3/2008 | Griffin et al. |
| 2008/0077168 A1 | 3/2008 | Nicholls et al. |
| 2008/0086149 A1 | 4/2008 | Diamant et al. |
| 2008/0086159 A1 | 4/2008 | Zweifler |
| 2008/0114298 A1 | 5/2008 | Cantor et al. |
| 2008/0200910 A1 | 8/2008 | Burger et al. |
| 2008/0214952 A1 | 9/2008 | Mir et al. |
| 2008/0255483 A1 | 10/2008 | Goldberg |
| 2008/0294183 A1 | 11/2008 | O |
| 2009/0004628 A1 | 1/2009 | Knutson |
| 2009/0093761 A1 | 4/2009 | Sliwa et al. |
| 2009/0112121 A1 | 4/2009 | Chuang et al. |
| 2009/0118638 A1 | 5/2009 | Schindlbeck et al. |
| 2010/0002910 A1 | 1/2010 | Delashmit, Jr. et al. |
| 2010/0004560 A1 | 1/2010 | Davison et al. |
| 2010/0010374 A1 | 1/2010 | Escutia et al. |
| 2010/0022910 A1 | 1/2010 | Lane et al. |
| 2010/0030100 A1 | 2/2010 | Tokumoto et al. |
| 2010/0049126 A1 | 2/2010 | Bronfeld et al. |
| 2010/0100005 A1 | 4/2010 | Mir et al. |
| 2010/0179455 A1 | 7/2010 | Nebrigic et al. |
| 2010/0252910 A1 | 10/2010 | Fujimori et al. |
| 2012/0089048 A1 | 4/2012 | Harish et al. |

FOREIGN PATENT DOCUMENTS

| | | |
|---|---|---|
| DE | 29620244 U1 | 2/1997 |
| DE | 29711006 U1 | 10/1997 |
| DE | 29811266 U1 | 11/1999 |
| DE | 102004025651 A1 | 12/2005 |
| EP | 0103664 B1 | 12/1986 |
| EP | 1399066 A1 | 3/2004 |
| EP | 1493386 A1 | 1/2005 |
| FR | 2747558 A1 | 10/1997 |
| GB | 2317113 A | 3/1998 |
| GB | 2321014 A | 7/1998 |
| GB | 2447369 A | 9/2008 |
| GB | 2450152 A | 12/2008 |
| JP | H09187487 A | 7/1997 |
| JP | 10014923 | 1/1998 |
| JP | 2000116629 A | 4/2000 |
| JP | 2007097980 A | 4/2007 |
| JP | 2008036299 A | 2/2008 |
| KR | 10-0792640 B1 | 1/2008 |
| WO | 1997024977 A1 | 7/1997 |
| WO | 1998041139 A1 | 9/1998 |
| WO | 0162150 A1 | 8/2001 |
| WO | 2004069301 A2 | 8/2004 |
| WO | 2007143377 A2 | 12/2007 |
| WO | 2008007906 A1 | 1/2008 |
| WO | 2009001347 A1 | 12/2008 |
| WO | 2009107806 A2 | 9/2009 |
| WO | 2009129272 A2 | 10/2009 |
| WO | 2010030965 A2 | 3/2010 |
| WO | 2010064211 A2 | 6/2010 |
| WO | 2010101621 A1 | 9/2010 |
| WO | 2010109461 A1 | 9/2010 |
| WO | 2011053018 A2 | 5/2011 |

(56) References Cited

FOREIGN PATENT DOCUMENTS

OTHER PUBLICATIONS

Journal of Cosmetic Dermatology: Kajal Babamiri and Reza Nassab: "The Evidence for Reducing the Pain of Administration of Local Anesthesia and Cosmetic Injectables", May 19, 2010, pp. 242-245.
Australian Journal of Advanced Nursing: "Effect of Local Refrigeration Prior to Venipuncture on Pain Related Responses in School Age Children": Ali Fakhr Movahedi et al.; Mar. 2006, vol. 24, No. 2, pp. 51-55.
Tintinalli's Emergency Medicine: A Comprehensive Study Guide: Chapter 36: Local and Regional Anesthesia: "Intradermal and Subdermal Anesthesia": Doublas C. Dillon and Michael A. Gibbs; Mar. 4, 2018.
IEEE: "Development of a Micro Lancet Needle Made of Biodegradable Polymer for Low-Invasive Medical Treatment"; S. Aoyagi, H. Izumi, T. Aoki and M. Fukuda; The 13th International Conference on Solid-State Sensors, Actuators and Microsystems, Seoul, Korea, Jun. 5-9, 2005; pp. 1195-1198.
Jacobs, L. Barry, "Cutaneous Pinprick Sensibility as a Screening Device," Diabetic Microvascular Complications Today, downloaded Oct. 17, 2012 from http://www.diabeticmctoday.com/HtmlPages/DMC0506/DMC0506_Neuro_Jacobs.html, 4 pages.
Takakura, Nobuari and Yajima, Hiroyoshi, "Double-Blind Placebo and Matched Needle," BMC Complementary and Alternative Medicine, Oct. 10, 2007, downloaded Oct. 17, 2012 from http://www.biomedcentral.com/1472-6882/7/31, 4 pages.
Mar. 22, 2013—(PCT) Search Report and Written Opinion—App PCT/US2012065990.
Oct. 1, 2013—(PCT) International Preliminary Report on Patentability (IPRP)—App PCT/US/2012/065990.
Dec. 5, 2014—(EP) Supplementary European Search Report—App 12852699.
Nov. 26, 2015—(EP) Office Action—App 12852699.
May 17, 2016—(EP) Office Action—App 12852699.
Mar. 13, 2013—(PA) Office Action—App 90227.
Apr. 24, 2018—(PE) Office Action—App. No. 000761-2014/DIN.
Jul. 10, 2018—(PE) Office Action—App. No. 000761-2014/DIN.

\* cited by examiner

FIG. 2
FIG. 3
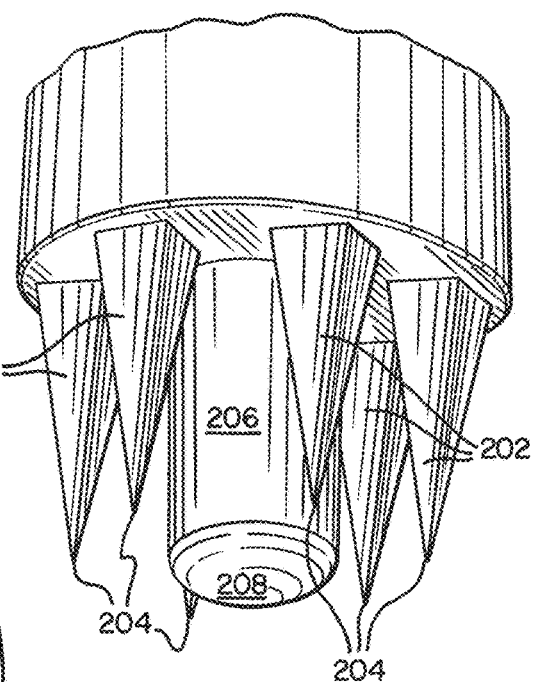
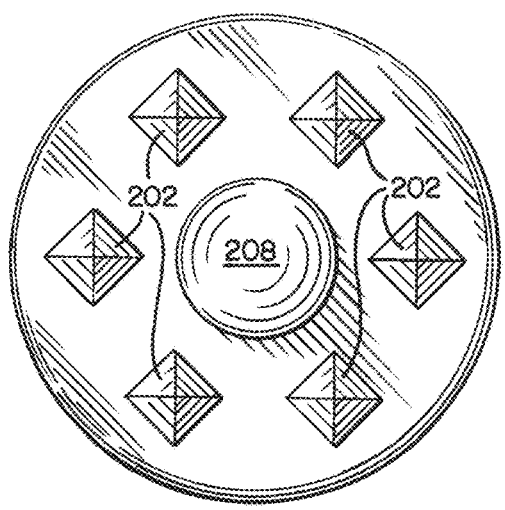
FIG. 4
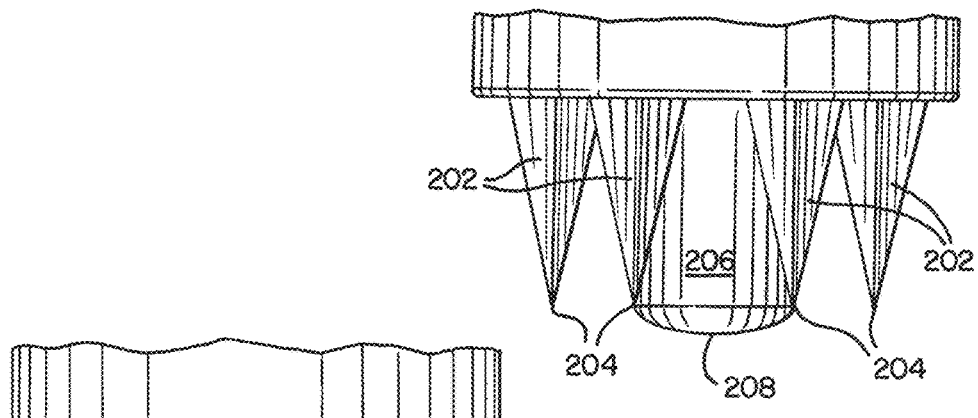
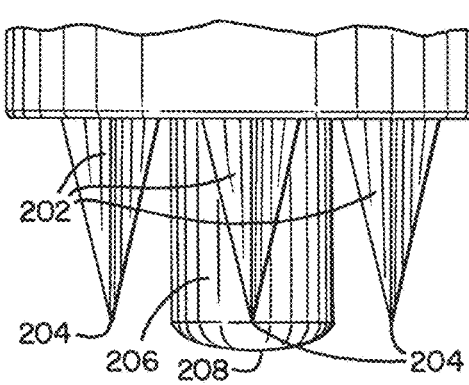
FIG. 5

ALLERGY TESTING DEVICE AND METHOD OF TESTING FOR ALLERGIES

RELATED APPLICATION

This Application is a continuation of U.S. application Ser. No. 14/689,686 filed on Apr. 17, 2015, which is a continuation of U.S. application Ser. No. 13/925,258 filed on Jun. 24, 2013, now U.S. Pat. No. 9,011,350, which is a continuation-in-part of U.S. application Ser. No. 13/308,111 filed on Nov. 30, 2011, now U.S. Pat. No. 8,469,900. The above applications are incorporated fully herein by reference in their entirety.

FIELD

This disclosure generally relates to reducing pain in a skin testing device system commonly used for applying test solution, such as liquid antigens, employed in skin testing for allergies, to patients' skin via skin test devices that have sharp pointed ends.

BACKGROUND

Skin testing to identify potential allergens that a patient may be allergic to is well known in many forms. The person conducting the skin testing may apply a relatively large number of test solutions to a patient's skin. To perform skin tests of this type, the person conducting the skin test typically places the skin test devices into a test solution such that a small amount of test solution adheres to the sharp pointed ends on the skin testing device via capillary attraction. The loaded skin test device is then pressed into a site on the patient's skin in a predetermined sequence. However, the sharp pointed ends of the skin test device may cause discomfort to some patients and much pain to other patients because the sharp pointed ends must penetrate the epidermis of the skin in order to get meaningful allergy test results. The discomfort and/or pain caused by the testing can be traumatic for the patient and disruptive to the nurse or doctor administering the testing.

BRIEF SUMMARY

In an exemplary embodiment, an allergy testing system is disclosed. The allergy testing system comprises a skin test device and a plurality of wells, each having a reservoir for receiving test solutions such as potential allergens or controls. The skin test device can have an elongated grip portion for holding the device. A plurality of legs extends from the grip, and the plurality of legs is spaced and oriented to contact a corresponding well containing the test solution. Each of the plurality of legs has a test head, and each test head has a plurality of elongated spike members. The elongated spike members have sharp ends configured to receive the test solution or potential allergen from a well, for example via capillary attraction, and to puncture a patient's skin to deliver the test solution or allergen. In addition, each test head has at least one touch activator. The touch activator is longer than the plurality of elongated spike members, such that during an allergy test, the touch activator comes into contact with the skin prior to the elongated spike members, causing the touch activator to activate nerve tissue that blocks pain transmission resulting in a reduction of discomfort and/or pain during testing. Each well reservoir is sized and oriented to receive a separate test head of the allergy testing applicator.

It will be appreciated by those skilled in the art, given the benefit of the following description of certain exemplary embodiments disclosed herein, that at least some of these embodiments have improved or alternative configurations suitable to provide enhanced benefits. These and other aspects, features and advantages of this disclosure or of certain embodiments of the disclosure will be further understood by those skilled in the art from the following description of exemplary embodiments taken in conjunction with the following drawings.

BRIEF DESCRIPTION OF THE DRAWINGS

To understand the present disclosure, it will now be described by way of example, with reference to the accompanying drawings in which:

FIG. 2 shows a magnified perspective view of a test head in accordance with an exemplary embodiment.

FIG. 3 shows a bottom view of the exemplary embodiment shown in FIG. 2.

FIG. 4 shows a front view of the exemplary embodiment shown in FIG. 2, wherein the rear view is a mirror image of FIG. 4.

FIG. 5 shows a right side view of the exemplary embodiment shown in FIG. 2, wherein the left side view is a mirror image of FIG. 5.

DETAILED DESCRIPTION OF CERTAIN EXEMPLARY EMBODIMENTS

Figure 1:
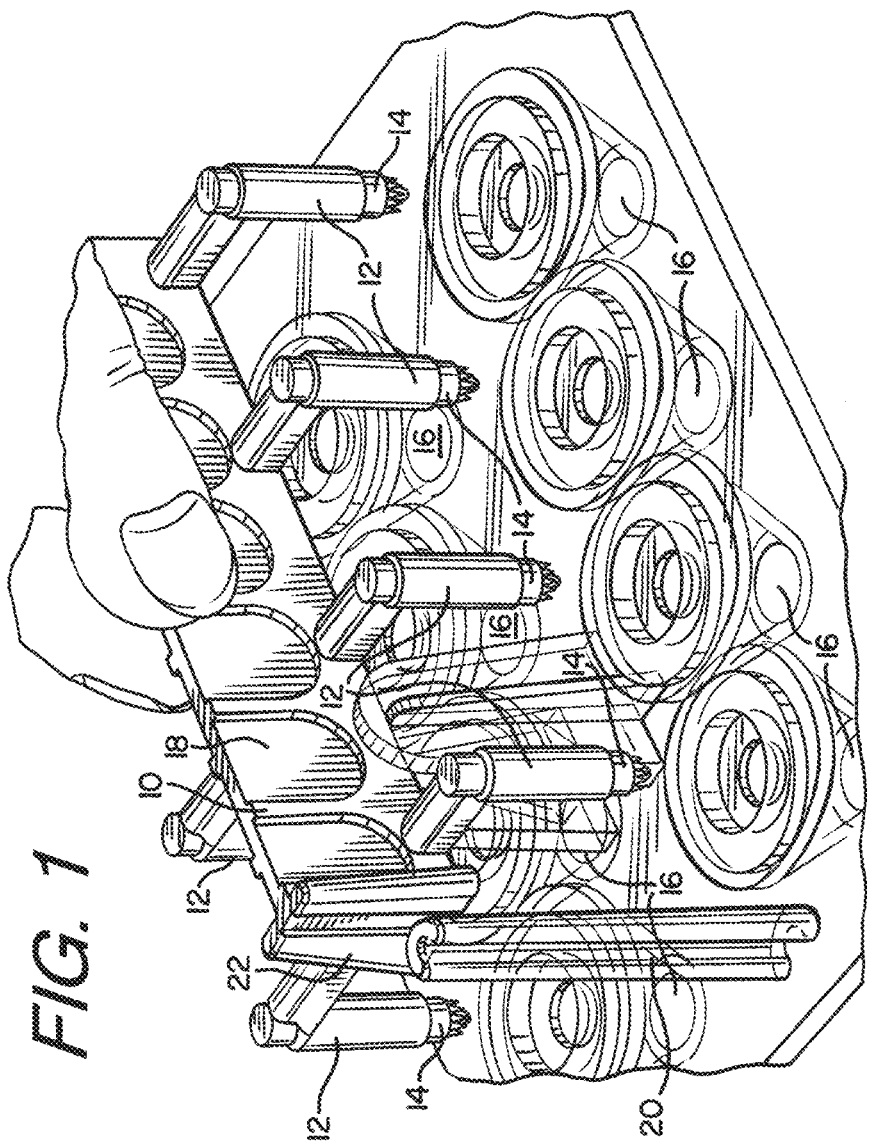
FIG. 1 shows a perspective view of a skin testing device in accordance with an exemplary embodiment.
Figure 6:
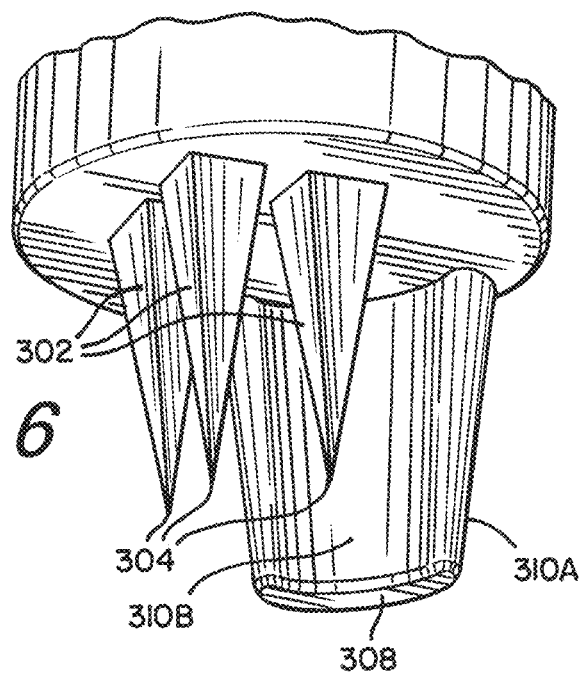
FIG. 6 shows a magnified perspective view of a test head in accordance with another exemplary embodiment.

While this disclosure is susceptible of embodiments in many different forms, there are shown in the drawings and will herein be described in detail exemplary embodiments with the understanding that the present disclosure is to be considered as an exemplification of the principles of the invention and is not intended to limit the broad aspect of the invention to the embodiments illustrated.

The embodiments disclosed herein are adaptations of the neurological gate-control theory to help reduce the amount of pain felt by the patient during allergy skin testing. The neurological gate-control theory involves the activation of nerve cells that block pain transmission resulting in pain suppression. This theory of pain acknowledges that activation of nerves that do not transmit pain signals can restrict transmission signals from pain fibers and inhibit pain perception.

As shown in FIG. 1, an exemplary skin test device 10 is shown having a plurality of test legs 12, although a device with a single leg is also contemplated as will be further described below in relation to FIG. 19. The skin test device 10 has an elongated grip portion 18 for holding the device. The test legs 12 extend from the grip 18 and are spaced and oriented to come into contact with corresponding wells 16 containing test solutions or allergens prior to being placed into contact with the skin of a patient. Each of the test legs 12 can be formed of a rigid plastic material, such that during testing the legs 12 do not flex relative to each other and the grip portion 18.

The skin test device 10 can be provided with an extension 22, which can be formed in the shape of a "T" on the elongated grip 18 to ensure that the skin test device 10 is placed into the wells 16 in the proper orientation as is disclosed in U.S. Pat. No. 5,792,071 to Hein, which is fully incorporated herein by reference.

Each elongated gripping portion 18 can be provided with one or more test heads 14, which are described in more detail below. Each of the test heads 14 are preferably shaped for being dipped into a series of wells 16. When the test heads 14 are placed into the wells 16, the test solution in the corresponding well 16 adheres to the corresponding test head 14 by capillary attraction. The test heads 14, which can be approximately 0.15 in. in diameter, are configured to be placed into contact with a patient's skin to apply the test solution and to determine whether the patient reacts positively to a particular allergen—indicating that the patient is allergic to that allergen.

The series of wells 16 each have a reservoir for receiving test solutions such as potential allergens or control solutions. A different test solution, such as an allergen or a control solution is placed into each reservoir, e.g., by using a dropper or any other suitable method known in the art. Each reservoir is sized and oriented to receive a separate test head 14 of the skin test device 10. The test wells 16 can be provided with guide tabs 20 for preventing the reversing of the skin test device 10 position in the wells 16.

Figure 20:
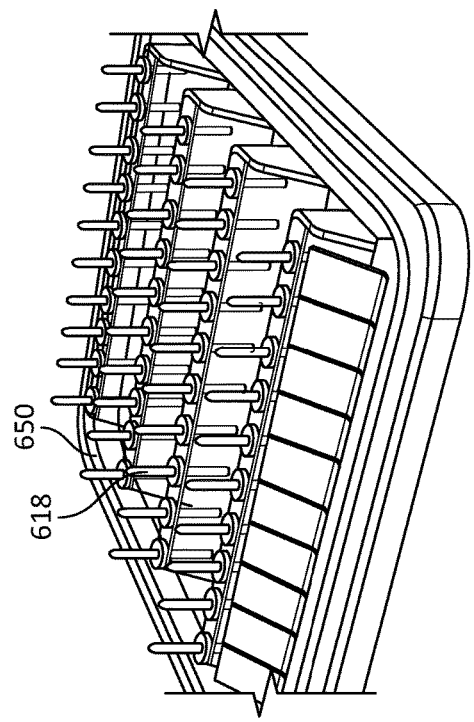
FIG. 20 illustrates an exemplary tray that can be used in conjunction with the embodiment shown in FIG. 19.
Figure 19:
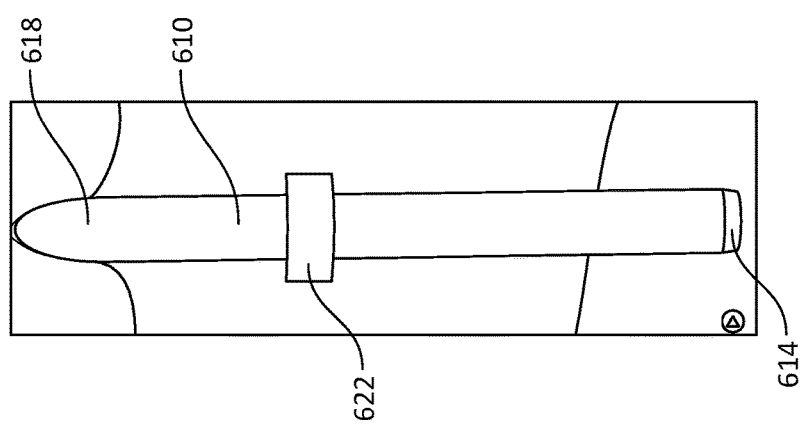
FIG. 19 depicts a skin testing device in accordance with another exemplary embodiment.

FIG. 19 shows an exemplary test device 610 which can be formed as a single leg or unitary testing device. The test device 610 can be formed with a singular test head 614, which can be formed with any of the exemplary test heads described herein. The test device 610 can include a collar 622 which ensures that the test head 614 extends to the appropriate level into the test solution in a respective well. The singular test head 614 can be used in conjunction with the tray 650 as depicted in FIG. 20. Tray 650 can be provided with a well holder configured to hold a plurality of test-solution wells for receiving various test solutions for loading multiple tests. One example of a tray and testing device is disclosed in U.S. Pat. No. 7,922,672, which is incorporated herein fully by reference.

FIG. 2 shows a perspective view of an exemplary test head, which can be used in conjunction with the skin test device 10 shown in FIG. 1. The test head of FIGS. 2-5 can be located at each end of the test legs 12 as shown in FIG. 1. The test head is provided with a plurality of elongated spikes 202 each having a sharp pointed end 204. The elongated spikes 202 can be formed in the shape of a pyramid or generally formed in the shape of a pyramid which may include other pyramid-like shapes, cones, or structures that converge to a single point to form a structure that is configured to penetrate skin to perform an allergy test. The elongated spikes 202 can also be formed with a base having a square shape. It is noted, however, that other suitable shapes of the elongated spikes 202 are also contemplated.

The exemplary test head shown in FIGS. 2-5 also has a touch activator formed as a touch post 206, which can be formed as a cylinder with a blunt convex top end 208. It is noted, however, that other suitable shapes of the touch post 206 are also contemplated. The blunt convex end 208 can be configured slightly longer than the elongated spikes 202 such that the convex end 208 of the touch post 206 makes contact with the patient's skin prior to the sharp pointed ends 204 of the elongated spikes 202.

As shown in FIG. 3, which is a bottom view of the exemplary test head, the test head can be provided with six elongated spikes 202; however, it is contemplated that different numbers of spikes can be used to accomplish acceptable allergy test results. For example, it is believed that the test head ideally may have between 3 and 6 spikes, but with smaller skin reactions with less than 6 spikes. The elongated spikes 202 can be arranged circumferentially around the touch post 206. However, other arrangements of the elongated spikes 202 and the touch post 206 are also contemplated. The arrangement shown in FIGS. 2-5 advantageously provides uniform loads of testing solutions on each test head during testing.

Figure 7:
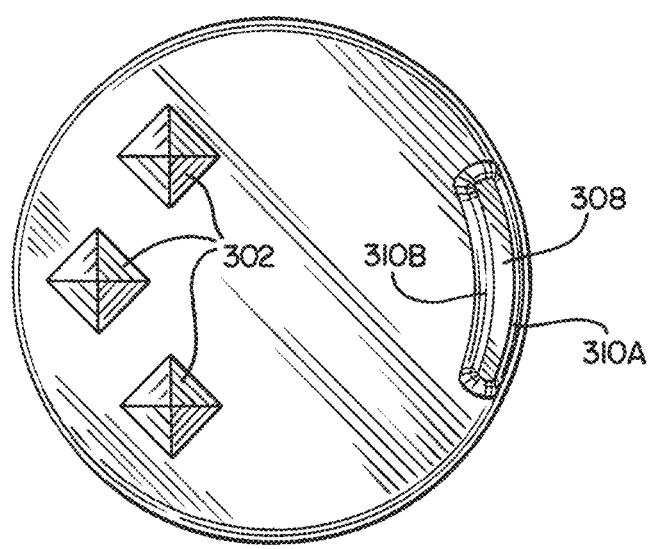
FIG. 7 shows a bottom view of the exemplary embodiment shown in FIG. 6.
Figure 8:
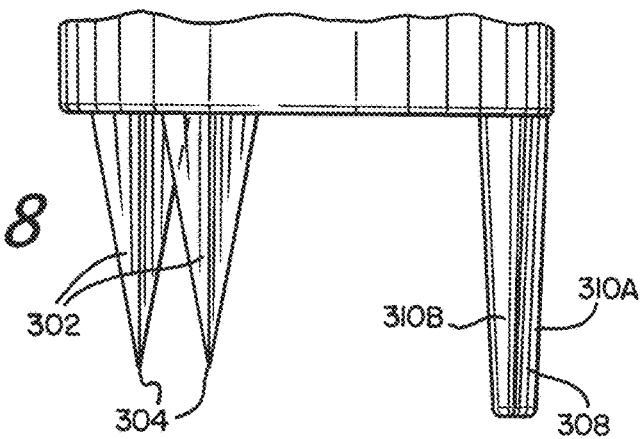
FIG. 8 shows a front view of the exemplary embodiment shown in FIG. 6.
Figure 9:
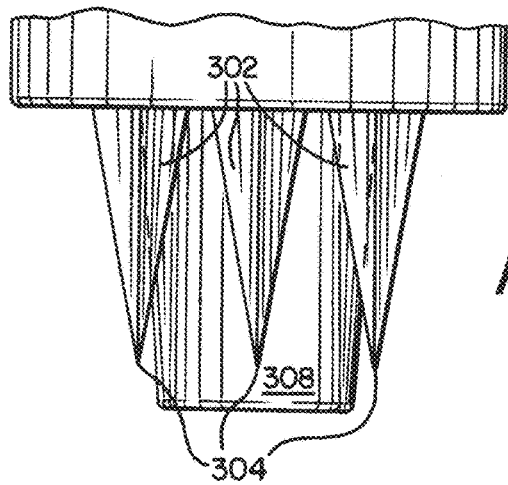
FIG. 9 shows a left side view of the exemplary embodiment shown in FIG. 6.
Figure 10:
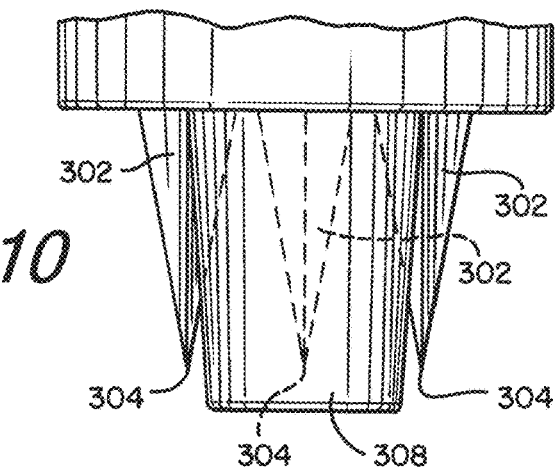
FIG. 10 shows a right side view of the exemplary embodiment shown in FIG. 6.
Figure 11:
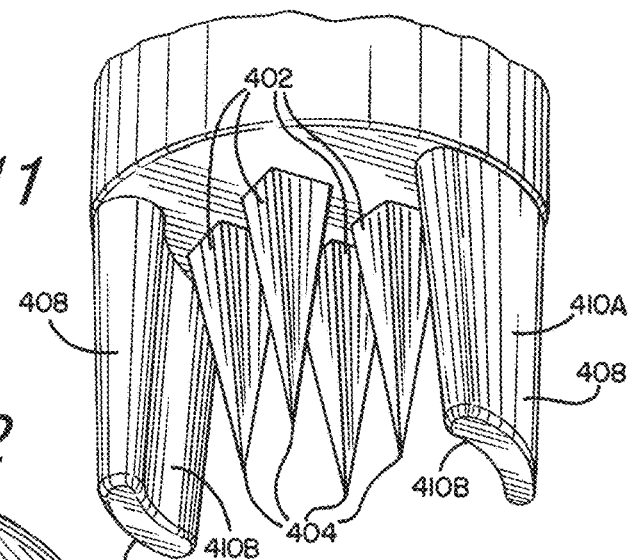
FIG. 11 shows a magnified perspective view of a test head in accordance with another exemplary embodiment.

FIGS. 6-10 show another embodiment of an exemplary test head, which can be used in conjunction with the skin test device 10 shown in FIG. 1. Again the exemplary head shown in FIGS. 6-10 can be located at each of the ends of the legs 12 shown in FIG. 1. FIG. 7 shows a bottom view of the exemplary embodiment of the test head in FIG. 6. This embodiment is similar to the embodiment shown in FIGS. 2-5. However, in this embodiment, the touch activator is formed as a touch collar 308. Also, as shown in FIGS. 6-10, the touch collar 308 is shaped with a convex outer surface 310A and a concave inner surface 310B and has a generally flat top surface.

In addition, the touch collar 308 is arranged off center on the test head on a first side, and the elongated spikes 302 are arranged on a second side. As shown in FIG. 7, the touch collar 308 is located radially outward from the center of the test head, and the elongated spikes 302 can be located radially outward from the center of the test head in the opposite direction from the touch collar 308. The elongated spikes 302 can be located as far away from the touch collar 308 as possible on the test head at a distance less than the diameter of the test head. In this embodiment, the placement of the elongated spikes are configured to conform to the circumference of the test head for ease of injection and to generally provide a maximum space between the touch activator 308 and the elongated spikes 302 to provide for a reduction of pain. This allows the elongated spikes 302 to penetrate the skin as much as possible, while maximizing the height of the touch activator 308 to provide for adequate pain reduction during testing. In addition, the outer convex surface 310A can generally follow the circumference of the test head. The concave inner surface 310B can follow the same curvature of the outer convex surface 310A. The touch collar 308 can also be formed with a tapered portion such that the touch collar is tapered from its base to its end portion. As shown in FIG. 7, a triangular arrangement is one suitable arrangement of the elongated spikes 302. However, again other arrangements of the elongated spikes 302 are also contemplated.

Figure 12:
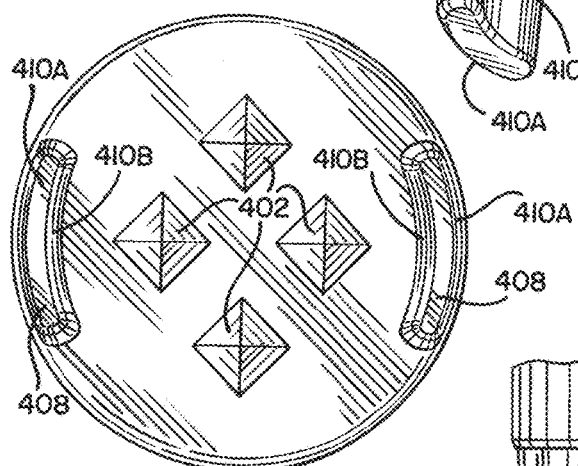
FIG. 12 shows a bottom view of the exemplary embodiment shown in FIG. 11.
Figure 13:
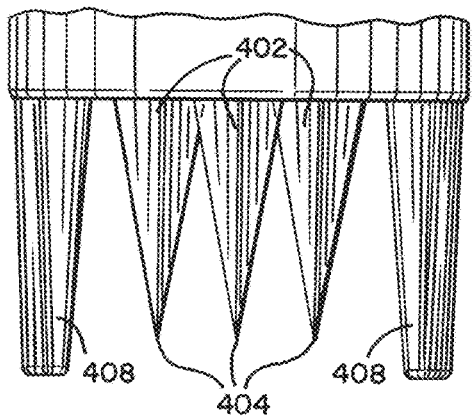
FIG. 13 shows a front view of the exemplary embodiment shown in FIG. 11, wherein the rear view is a mirror image of FIG. 13.
Figure 14:
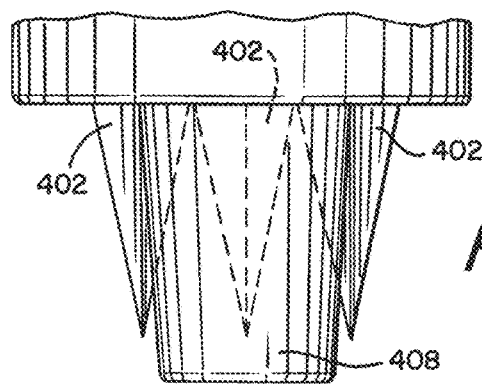
FIG. 14 shows a right side view of the exemplary embodiment shown in FIG. 11, wherein the left side view is a mirror image of FIG. 14.
Figure 15:
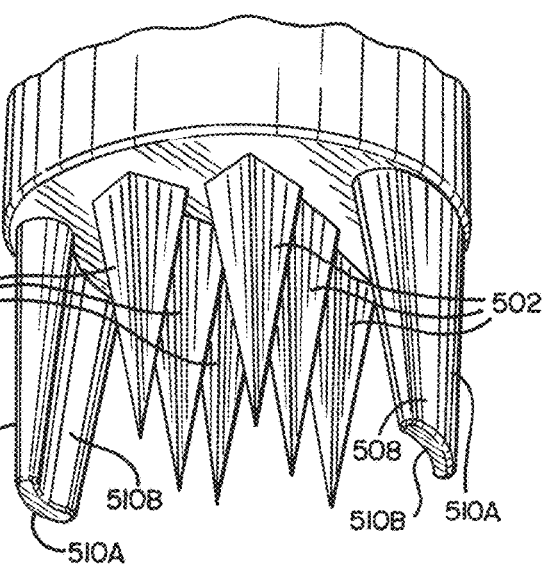
FIG. 15 shows a magnified perspective view of a test head in accordance with another exemplary embodiment.
Figure 16:
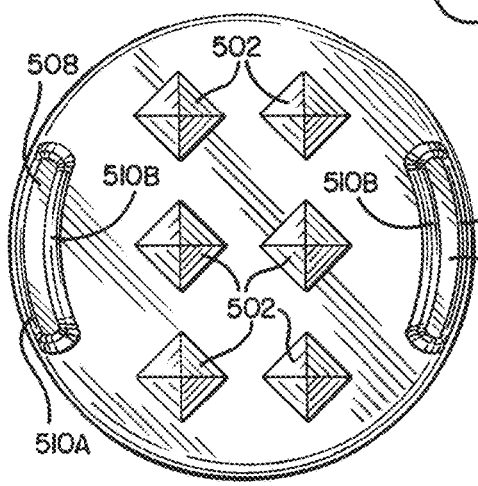
FIG. 16 shows a bottom view of the exemplary embodiment shown in FIG. 15.
Figure 17:
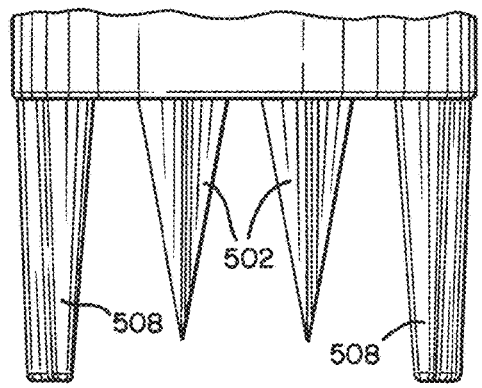
FIG. 17 shows a front view of the exemplary embodiment shown in FIG. 15, wherein the rear view is a mirror image of FIG. 17.
Figure 18:
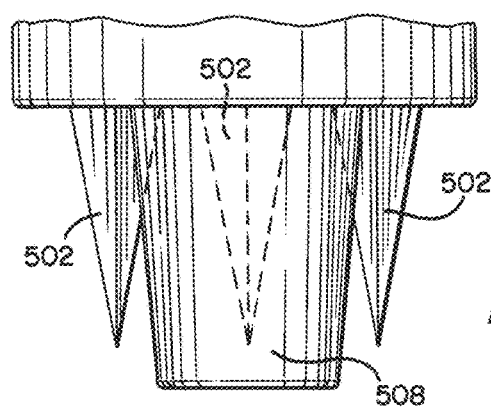
FIG. 18 shows a right side view of the exemplary embodiment shown in FIG. 15, wherein the left side view is a mirror image of FIG. 18.

FIGS. 11-14 show another exemplary test head, which can be used in conjunction with the skin test device 10 shown in FIG. 1. This embodiment is similar to the embodiment shown in FIGS. 6-10. However, in this embodiment two touch activators formed as touch collars 408 are arranged off center on the test head or radially outward from the center and on opposite sides of the test head, and the elongated spikes 402 are arranged radially inward closer to the center of the test head. As shown in FIG. 12, the test head can be formed with four elongated spike members 402 having sharp pointed ends 404 that are arranged in a diamond shaped pattern. The elongated spikes 402 can be arranged at a distance from the touch collars 408, which is less than the radius of the test head. Additionally, like in the embodiment shown in FIGS. 6-10, the outer convex surfaces 410A of the touch collars 408 can generally follow the circumference of the test head. Likewise, the concave inner surfaces 410B can follow the same curvature of the outer convex surfaces 410A. The touch collars 408 can also be formed with a tapered portion.

FIGS. 15-18 show another exemplary test head, which can be used in conjunction with the skin test device 10 shown in FIG. 1. This embodiment is similar to the embodiment shown in FIGS. 11-14; however, in this embodiment there are six elongated spikes 502 arranged in two rows of three. The elongated spikes 502 can be arranged at a distance from the touch collars 508, which is less than the radius of the test head. Additionally, like in the embodiment shown in FIGS. 11-14, the outer convex surfaces 510A of touch collars 508 generally follow the circumference of the test head and the inner concave surfaces 510B can follow the same curvature. The touch collars 508 can also be formed with a tapered portion.

Again, the shapes and arrangements of the components described in the embodiments above are merely exemplary; other shapes and arrangements are also contemplated. In each of the embodiments shown in FIGS. 2-18, the touch activators are longer than the elongated spikes, such that the touch activators always come into contact with the patient's skin prior to the elongated spikes. This is necessary to provide adequate pain gate control or activation of nerve cells that block pain transmission, which results in pain suppression.

In the above embodiments, each of the elongated spikes can be manufactured at the same length and can all be the same length shorter than the touch activator(s). In addition, in the above embodiments, the touch activators can be manufactured at the same height so that the touch activators are the same length longer than the elongated spikes. However, arranging the elongated spikes at different lengths on the same or different test heads is also contemplated. Also length variances may occur due to manufacturing capabilities. However, it is noted that setting the touch activators at the same length as the elongated spikes will still produce satisfactory wheal sizes or allergy test results, but without the relief of pain to the patient.

The testing devices can be formed of a rigid plastic such as an acrylic polymer. However, other suitable materials are also contemplated. Forming each of the test legs 12 and the test heads including the touch activators and the elongated spikes of a rigid plastic material may also provide more consistent and readable test results. By forming the testing devices of a rigid plastic, during testing the legs 12 do not flex relative to each other and the grip portion 18, which provides more consistent test results. In this way, the testing device is configured such that the test heads and the legs maintain the same spacing during testing. Also providing rigid spikes and touch activators may provide a more uniform penetration of the elongated spikes into the skin, which allows for a more even distribution of the test solution into the skin providing more readable reactions.

Forming each of the test legs 12 and the test heads including the touch activators and the elongated spikes of a rigid plastic material may also provide more uniform pain mitigation across the skin testing area. Because the test heads, the touch activators, and the elongated spikes all remain in a constant relationship with respect to one another, the pain mitigation effect remains constant in each location of skin penetration. This provides more effective pain management and allows the patient to be more comfortable during the testing.

Referring back to FIG. 1, in one exemplary process for using the system, the health care administrator of the test may place the test heads 14 into the series of wells 16. The guide 20 in conjunction with the extension 22 on the elongated grip 18 ensures that the skin testing device 10 is placed into the wells 16 in the proper orientation reducing the possibility of testing errors. The test heads 14 are configured to receive test solutions, such as potential allergens or control solutions, from the series of wells 16. During use, the test heads 14 are pressed firmly into contact with the skin of the patient. The test heads can be applied to the skin using a rocking motion such that the skin test device 10 is moved back and forth to provide the desired amount of elongated spike penetration into the patient's skin. The touch activators come into contact with the skin before the elongated spikes, such that the touch activators activate nerve tissue that blocks pain, resulting in a reduction of pain and/or discomfort during testing. During use, the elongated spikes of the test heads 14 puncture the skin and administer the allergens, but, the patient will feel less pain from the elongated spikes. The test administrator may subsequently interpret the results to determine whether the patient is allergic to a particular allergen.

A similar testing method can be implemented using the allergy testing device 610 depicted in FIG. 19. However in this example, multiple testing devices 610 may be used to test multiple test sites for various allergenic reactions.

It is also contemplated that the test heads can be loaded with solution using other techniques, such as by individually loading the test heads with a series of droppers. The Dip N' Touch® liquid dispenser offered by Lincoln Diagnostics Inc. is another example test solution loading technique. This technique involves loading individual test heads using a modified dropper having a wider opening near the end. In this way, the administrator of the test can simply touch the test head with the solution in the end of the dropper to load the particular test head with solution.

During the testing, the touch activators located on the test heads, will pick up solution along with the elongated spikes when the test heads are placed in the dipwell. In this way, slightly less test solution is picked up than in other allergy testing devices, and the touch activators interact with the elongated spikes in such a way that a very uniform load results. The arrangement of the touch activators and the spikes on the test heads results in a uniform load due to the capillary attraction of the test solution on both the touch activator and the elongated spikes.

The embodiment in FIG. 19 utilizes minimal material, and therefore, may provide cost savings for the purchasing allergist. In particular, the single leg test device 610 enables the allergist to test skin at a lower cost per test site. However, conducting eight tests simultaneously using the example shown in FIG. 1 may have certain economic advantages. For example, if the allergist has to conduct many tests, the example shown in FIG. 1 may be a more viable option to administer tests quicker and more efficiently.

Another potential advantage of the example shown in FIG. 19 is that test sites can be placed further apart, which may provide more readable results. However, the embodiment shown in FIG. 1 may provide virtually painless skin testing with large and easy to read reactions that may have less variation between users than the testing conducted with the single leg device shown in FIG. 19.

In the exemplary embodiments disclosed in FIGS. 2-18, the touch activators activate nerve cells that inhibit pain, while sharp refined points apply the test solution. The refined points provide well-defined wheals with very little tissue trauma. This design provides high sensitivity, high specificity, and low variability in results with little pain felt by the patient. The test head configuration described herein may also decrease skin trauma.

It has been discovered that there is an ideal distance between the top of the touch activators and the ends of the elongated spikes for realizing pain suppression, while also gaining sufficient penetration of the pointed ends. Lengths of touch activators in the range of approximately 0.005 in. to 0.010 in. longer than the elongated spikes (when measured from the top of the touch activator to the tip or sharp point of the elongated spikes) provide acceptable results. As discussed below, providing touch activators that are 0.007 in. to 0.010 in. longer than the elongated spikes provided the best test results for the disclosed embodiments while suppressing meaningful pain felt by the subjects. As further discussed below, a difference in length of 0.010 in. between the touch activators and elongated spikes provided the best observed results. However, it may be the case that different distances between the top of the touch activators and the ends of the elongated spikes are suitable in other arrangements and configurations of allergy skin testing devices. The test results are described below in more detail.

In the first test, the top of the touch activators were manufactured flush with the ends of the elongated spikes. No pain relief was observed, but the tests provided satisfactory wheal sizes from histamine at 1 mg/ml.

In the second test, the top of the touch activators were manufactured 0.003 in. longer than the ends of the elongated spikes. No pain relief was observed; however, the tests provided satisfactory wheal sizes from histamine.

In the third test, the top of the touch activators were manufactured 0.005 in. longer than the ends of the elongated spikes. Some reduction of pain was observed, and the tests provided satisfactory wheal sizes.

In the fourth test, the top of the touch activators were manufactured 0.007 in. longer than the ends of the elongated spikes. A meaningful reduction of pain was observed, and the tests provided satisfactory wheal sizes.

In the fifth test, the top of the touch activators were manufactured 0.010 in. longer than the ends of the elongated spikes. Virtually no pain was observed by the subjects, and the tests provided satisfactory wheal sizes that averaged 7 mm in diameter with very low variation in wheal sizes.

Incorporating the touch activators on the same test head as the elongated spikes provides many benefits. Previously, many allergists placed drops of extract on the skin and then pricked through the skin at the drops with a metal point; however, this practice is no longer widely used. Most doctors handling allergy diagnosis use self-loading devices that involve immersion of the points into testing solutions, allowing the points to load via capillary attraction. By incorporating the pain suppresser near the pain producer on the same test head, the skin testing devices can be immersed easily into the wells 16 shown in FIG. 1. The dimensions of the exemplary skin testing devices disclosed herein can remain the same as those on other skin testing devices currently manufactured, such as those by the current assignee Lincoln Diagnostics, Inc. Consequently, the elongated spikes of the skin testing devices disclosed herein can be dipped into the currently existing wells.

Also by incorporating the touch activator and the elongated spikes on the same test head, it is simpler to inspect the devices for compliance with the critical length dimensions described above and to package them. In contrast, the use of pain suppressers separated from each test head would make inspection more complex and require larger and more complex unit containers.

Additionally including the elongated spikes and the touch activators on the same test head provides a more compact and simplified design. The closer the touch activator is located to the elongated spikes, the greater the ability of the touch activator to inhibit pain. In other words, the required surface area of the touch activator to inhibit pain is proportional to the distance to the elongated spikes, which means that the greater the distance between the elongated spikes and the touch activator, the larger the surface area the touch activator must be for pain mitigation. Therefore, including the touch activator on the test head permits distance between the elongated spikes and the touch activator to be smaller and subsequently permits the surface area of the touch activator to also be smaller, which provides for a more compact design of the testing device.

Additionally, forming the skin test device of a rigid plastic material and including the touch activators on the same test head as the elongated spikes also provides for certain advantages. For example, a precise control of the distance between the length of the touch posts and the length of the points when contacting the skin can be achieved. The touch activator and the elongated spikes can be configured to maintain the same spacing during testing. Also a high level of pain control over the entire length of the testing device can be established because each test head contains a touch post. Otherwise without these features, the touch sensation may vary from site to site due to the variability of skin contour and subsequent penetration of the elongated spikes.

Devices that employ the pain suppressers separated from the test head are difficult and impractical to use with existing wells containing test solutions. In these devices, it would also be difficult to accomplish reliable self-loading of allergen extracts via capillary attraction. Additionally, less plastic is used when the touch activator and the elongated spikes are incorporated onto the same test head. This provides a skin test device that is less expensive to manufacture.

Also, for the skin testing devices disclosed herein, the amount of test solution is less in volume than that for the previous skin testing devices because of the arrangement of the elongated spikes and the touch activators. The end result is more test sites from a 5 ml vial of test solutions, such as allergens, allergenic extracts, and controls.

One exemplary embodiment includes an allergy testing system having a skin test device. The skin test device can include an elongated grip portion for holding the device and a plurality of legs extending from the grip. The plurality of legs can be spaced and oriented to interact with a plurality of wells containing test solutions. Each of the plurality of legs can have a test head, each test head can include a plurality of elongated spikes each having a sharp end configured to receive the test solution from a well and to puncture skin to deliver the test solution. Each test head may include at least one touch activator. The touch activator can be longer than the plurality of elongated spikes, such that during an allergy test, the touch activator can be configured to come into contact with the skin prior to the elongated spikes, to cause the touch activators to activate nerve tissue that suppresses transmission of pain, resulting in a reduction of pain during testing. The plurality of legs can be configured such that the test heads maintain the same spacing during testing. Both the touch activator and the plurality of elongated spikes can be configured to come into contact with the test solutions and are configured to receive the test solutions by capillary attraction. The skin test device can be formed rigid to maintain the same spacing between each of the plurality of legs during testing. The skin test device can be configured to provide uniform pain management across the skin. The test heads can be configured to provide uniform penetration of the elongated spikes on the skin. The spacing between the elongated spikes and the touch activator can be configured to remain constant.

In another example, a skin test device can include a grip portion for holding the skin test device and at least one leg extending from the grip portion. Each leg can be oriented to interact with a well containing a test solution. The at least one leg can have a test head having a plurality of elongated spikes and at least one touch activator. The plurality of elongated spikes can each have a sharp end configured to receive the test solution from a well and to puncture skin for delivering the test solution. The touch activator and the elongated spikes can be configured to maintain the same spacing during testing. The touch activator can be longer than the plurality of elongated spikes, such that during an allergy test, the touch activator can be configured to come into contact with the skin prior to the elongated spikes, to cause the touch activator to activate nerve tissue that suppresses pain, resulting in a reduction of pain during testing. The skin test device can be formed rigid. Both the touch activator and the plurality of elongated spikes can be configured to come into contact with the test solutions and can be configured to receive the test solutions by capillary attraction. The spacing between the elongated spikes and the touch activator can be configured to remain constant. The skin test device can be configured to provide uniform pain management across the skin. Test head can be configured to provide uniform penetration for the elongated spikes on the skin.

Given the benefit of the above disclosure and description of exemplary embodiments, it will be apparent to those skilled in the art that numerous alternative and different embodiments are possible in keeping with the general principles of the invention disclosed here. Those skilled in this art will recognize that all such various modifications and alternative embodiments are within the true scope and spirit of the invention. The appended claims are intended to cover all such modifications and alternative embodiments. It should be understood that the use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc.

What is claimed is:

1. An allergy testing system comprising:
   a tray comprising:
      a plurality of wells containing test solutions;
      at least one guide tab;
   a skin test device comprising:
      an elongated grip portion for holding the skin test device;
      an extension from the elongated grip portion; and
      a plurality of legs extending from the elongated grip portion, the plurality of legs spaced and oriented to interact with the plurality of wells of the tray containing test solutions; wherein each of the plurality of legs has a test head, each test head having a center and comprising a plurality of elongated spikes each having a sharp end configured to receive the test solution from a well and to puncture skin to deliver the test solution, each test head further comprising at least two touch activators positioned radially outward from the center of the test head and on opposite sides of the test head, wherein the at least two touch activators are longer than the plurality of elongated spikes and the plurality of elongated spikes are arranged radially inward to the center of the test head, configured to cause the at least two touch activators to activate nerve tissue that suppresses transmission of pain, resulting in a reduction of pain during testing and the plurality of legs being configured such that the test heads maintain the same spacing during testing;
   wherein each of the plurality of wells has a reservoir sized and oriented to receive the test heads.

2. The allergy testing system of claim 1, wherein the at least two touch activators and the plurality of elongated spikes are configured to come into contact with the test solutions and are configured to receive the test solutions by capillary attraction.

3. The allergy testing system of claim 1, wherein the skin test device is formed rigid to maintain the same spacing between each of the plurality of legs during testing.

4. The allergy testing system of claim 1, wherein the skin test device is configured to provide uniform pain management across the skin.

5. The allergy testing system of claim 1, wherein the test heads are configured to provide uniform penetration of the elongated spikes on the skin.

6. The allergy testing system of claim 1, wherein the spacing between adjacent elongated spikes is configured to remain constant.

7. The allergy testing system of claim 1, wherein the at least two touch activators are touch collars, each having an outer convex surface that follows the circumference of the test head.

8. A skin test device comprising:
   an elongated grip portion for holding the skin test device;
   an extension from the elongated grip portion; and
   a plurality of legs extending from the elongated grip portion, the plurality of legs spaced and oriented to interact with a plurality of wells containing test solutions; wherein each of the plurality of legs has a test head having a center and comprising a plurality of elongated spikes and at least two touch activators; and wherein the at least two touch activators are longer than the plurality of elongated spikes and are configured to cause the at least two touch activators to activate nerve tissue that suppresses transmission of pain, resulting in a reduction of pain during testing, wherein the at least two touch activators are positioned radially outward from the center of the test head and on opposite sides of the test head, and the plurality of elongated spikes are arranged radially inward closer to the center of the test head.

9. The skin test device of claim 8 wherein the skin test device is formed rigid.

10. The skin test device of claim 8, wherein the at least two touch activators and the plurality of elongated spikes are configured to come into contact with the test solutions and are configured to receive the test solutions by capillary attraction.

11. The skin test device of claim 9, wherein plurality of legs are formed rigid to maintain the same spacing.

12. The skin test device of claim 8, wherein the test heads provide uniform pain management across the skin.

13. The skin test device of claim 8, wherein the test heads are configured to provide uniform penetration for the elongated spikes when placed on skin.

14. The skin test device of claim 8, wherein the spacing between adjacent elongated spikes is configured to remain constant.

15. The skin test device of claim 8, wherein the at least two touch activators are touch collars, each having an outer convex surface that follows the circumference of the test head.

16. A skin test device comprising:
a grip portion for holding the skin test device;
at least one leg extending from the grip portion, each leg oriented to interact with a well containing a test solution; and
wherein the at least one leg has a test head having a center and comprising a plurality of elongated spikes and at least two touch activators, the plurality of elongated spikes each have a sharp end configured to receive the test solution from the well and to puncture skin for delivering the test solution, the at least two touch activators being positioned radially outward from the center of the test head and on opposite sides of the test head and the plurality of elongated spikes being arranged radially inward closer to the center of the test head, and the at least two touch activator is longer than the plurality of elongated spikes, such that during an allergy test, the at least two touch activators are configured to come into contact with the skin prior to the elongated spikes, to cause the at least two touch activator to activate nerve tissue that suppresses pain, resulting in a reduction of pain during testing.

17. The skin test device of claim 16 further comprising a rigid body.

18. The skin test device of claim 16, wherein the at least two touch activator and the plurality of elongated spikes are configured to come into contact with the test solutions and are configured to receive the test solutions by capillary attraction.

19. The skin test device of claim 16, wherein the spacing between adjacent elongated spikes is configured to remain constant.

20. The skin test device of claim 16, wherein the test head is configured to provide uniform penetration of the elongated spikes on the skin.

21. The skin test device of claim 16, wherein the at least two touch activators are touch collars, each having an outer convex surface that follows the circumference of the test head.

* * * * *